(12) United States Patent
Evans et al.

(10) Patent No.: US 8,046,173 B2
(45) Date of Patent: Oct. 25, 2011

(54) METHOD FOR IDENTIFYING SUB-SEQUENCES OF INTEREST IN A SEQUENCE

(75) Inventors: Scott Charles Evans, Burnt Hills, NY (US); Stephen Francis Bush, Latham, NY (US); Andrew Soliz Torres, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 773 days.

(21) Appl. No.: 12/043,609

(22) Filed: Mar. 6, 2008

(65) Prior Publication Data

US 2008/0270439 A1 Oct. 30, 2008

Related U.S. Application Data

(62) Division of application No. 10/858,744, filed on Jun. 2, 2004, now abandoned.

(51) Int. Cl.
*G06F 19/00* (2011.01)
(52) U.S. Cl. ........................................................ 702/19
(58) Field of Classification Search .................... None
See application file for complete search history.

(56) References Cited

U.S. PATENT DOCUMENTS

| | | | | |
|---|---|---|---|---|
| 5,136,686 | A * | 8/1992 | Koza ............................... | 706/13 |
| 5,455,577 | A * | 10/1995 | Slivka et al. .................... | 341/51 |
| 5,617,552 | A * | 4/1997 | Garber et al. ..................... | 711/1 |
| 5,703,581 | A * | 12/1997 | Matias et al. ................... | 341/67 |
| 5,977,890 | A * | 11/1999 | Rigoutsos et al. .............. | 341/55 |
| 6,373,971 | B1 * | 4/2002 | Floratos et al. ............... | 382/129 |
| 6,473,757 | B1 * | 10/2002 | Garofalakis et al. ................ | 1/1 |
| 7,043,371 | B2 * | 5/2006 | Wheeler ......................... | 702/19 |
| 2004/0249574 | A1 | 12/2004 | Tishby et al. | |

OTHER PUBLICATIONS

Evans et al. (GE Global Research Technical Information Series Oct. 2002; Kolmogorov Complexity Estimation and Analysis).*
Troyanskaya et al. Bioinformatics (2002) vol. 18, No. 5, pp. 679-688.*
O. G. Troyanskaya et al.; Title: "Sequence Complexity Profiles of Prokaryotic Genome Sequences: A fast Algorithm for Calculating Linguistic Complexity"; BIOINFORMATICS; vol. 18 No. 5 2002; pp. 679-688.
Scott C. Evans; Title: "Kolmogorov Complexity Estimation and Application for Information System Security"; Rensselaer Polytechnic Institute; Troy, New York; Jul. 2003.
Moses Charikar et al., "Approximating the Smallest Grammar: Kolmogorov Complexity in Natural Models", Proceedings of Annual ACM Symposium, Feb. 20, 2002, pp. 792-801.
S.C. Evans and S.F. Bush, "Symbol Compression Ratio for String Compression and Estimation of Kolmogorov Complexity", 2001CRD159, Class 1, Nov. 2001, 16 Pages.
Craig G. Nevill-Manning and Ian H. Witten, "On-Line and Off-Line Heuristics for Inferring Hierarchies of Repetitions in Sequences", Proceedings of the IEEE, vol. 88, No. 11, Nov. 2000, pp. 1745-1755.
Alberto Apostolico and Stefano Lonardi, "Off-Line Compression by Greedy Textual Substitution", Proceedings of the IEEE, vol. 88, No. 11, Nov. 2000, pp. 1733-1744.

* cited by examiner

*Primary Examiner* — Lori A Clow
(74) *Attorney, Agent, or Firm* — Fletcher Yoder

(57) ABSTRACT

The present technique provides for the analysis of a data series to identify sequences of interest within the series. The analysis may be used to iteratively update a grammar used to analyze the data series or updated versions of the data series. Furthermore, the technique provides for the calculation of a minimum description length heuristic, such as a symbol compression ratio, for each sub-sequence of the analyzed data sequence. The technique may then compare a selected heuristic value against one or more reference conditions to determine if additional iteration is to be performed. The grammar and the data sequence may be updated between iterations to include a symbol representing a string corresponding to the selected heuristic value based upon a non-termination result of the comparison. Alternatively, the string corresponding to the selected heuristic value may be identified as a sequence of interest based upon a termination result of the comparison.

9 Claims, 3 Drawing Sheets

SEQ. ID NO: 1

ATGTCATTACGCATTAAACAAGAAGCCCTTACTTTTGACGATGTTCTACTCGTCCCAGCTCACTCAACTGTGCTTCCAAA
TACTGCCAACCTTTCAACTCAACTTACTAAAGAAATTCGTTTAAATATCCCAATGCTTTCAGCAGCAATGGATACCGTAA
CTGAAACCAAACTTGCGATCTCTTTAGCACAAGAAGGCGGTATTGGCTTTATTCATAAAAATATGACGATCGAACGCCAA
GCAGATCGCGTGCGTAAAGTAAAAAAATTCGAAAGTGGTATCGTTTCTGAACCAGTAACTGTTTTACCAAATTTAACGCT
TGCCGAACTTGCTGAAATGGTGAAGAAAAACGGATTTGCGGGCTACCCTGTTGTAGATGGGGAAAATAATTTAATCGGTA
TCATTACTGGCCGTGATACACGTTTCGTAAAAGATTTAAGCAAAACAGTTTCACAAGTAATGACGAAAAAAGAAGACTTG
GTGACCGTAAAAGAAGGGGCGAGTCGCGAAGAAATTTTGGAATTAATGCATCAACACCGTGTTGAAAAAGTATTAGTGGT
TAATGATAGTTTCAAACTTAAAGGTATGATTACCGTTAAAGACTTCCAAAAAGCAGAACAAAAACCAAATGCATGTAAAG
ATGAATTCGGTCGTTTACGTGTCGGTGCGGCTGTAGGTGCAGGTGCTGGCAACGAACAACGTATTGATGCCTTAGTGAAA
GCAGGCGTAGATGTACTATTAATTGATTCTTCTCACGGTCACTCAGAAGGCGTATTACAACGCGTTCGTGAAACTCGTGC
AAAATATCCAAATTTGCCTATCGTTGCAGGTAACGTAGCAACGGCTGAAGGCGCAATTGCATTAGCAGACGCAGGTGCAA
GTGCTGTAAAAGTAGGTATTGGTCCTGGTTCAATTTGTACAACTCGTATTGTAACTGGCGTAGGTGTTCCACAAATTACC
GCTATCGCAGATGCAGCTGCTGCATTAAAAGATCGTGGTATTCCTGTAATTGCTGACGGTGGTATCCGTTTCTCTGGCGA
TATTGCAAAAGCTATCGCTGCTGGTGCAAGCTGTGTAATGGTTGGCTCGATGTTTGCGGGTACAGAAGAGGCTCCAGGTG
AAATCGAACTTTATCAAGGTCGTGCATTTAAATCTTACCGTGGTATGGGCTCATTAGGTGCCATGGCGAAAGGCTCATCA
GACCGTTATTTCCAATCGGATAACGCGGCAGATAAACTCGTACCGGAAGGTATTGAAGGCCGTATTCCATATAAAGGTTA
CTTAAAAGAAATCATCCACCAACAAATGGGTGGCTTACGTTCTTGTATGGGCTTAACGGGCTGTGCAACTATTGATGAAC
TACGCACCAAAGCGGAATTTGTTCGCATTAGCGGTGCAGGCATTAAAGAAAGCCACGTTCACGATGTTGCTATTACTAAA
GAAGCACCTAACTATCGTATGGGCTAAATGACAAATATCCACTATCACAAAATCCTAATCCTCGACTTTGGTTCACAATA
CACTCAACTGATTGCGCGTCGTGTGCGTGAAATCGGTGTGTACTGCGAACTTTGGGCTTGGGATGTAACCGAACAAAAAT
CCGTGAATTTGCTCCCG

. . .

SEQ. ID NO: 2

AACTTTATCAAGGTCGTGCATTTAAATCTTACCGTGGTATGGGCTCATTAGGTGCCATGGCGAAAGGCTCATCAGACCGT
TATTTCCAATCGGATAACGCGGCAGATAAACTCGTACCGGAAGGTATTGAAGGCCGTATTCCATATAAAGGTTACTTAAA
AGAAATCATCCACCAACAAATGGGTGGCTTACGTTCTTGTATGGGCTTAACGGGCTGTGCAACTATTGATGAACTACGCA
CCAAAGCGGAATTTGTTCGCATTAGCGGTGCAGGCATTAAAGAAAGCCACGTTCACGATGTTGCTATTACTAAAGAAGCA
CCTAACTATCGTATGGGCTAAATGACAAATATCCACTATCACAAAATCCTAATCCTCGACTTTGGTTCACAATACACTCA
ACTGATTGCGCGTCGTGTGCGTGAAATCGGTGTGTACTGCGAACTTTGGGCTTGGGATGTAACCGAACAACAAATCCGTG
AATTTGCTCCAACGGGTATCATTCTTTCTGGCAGTCCTGAAAGCAACTGAAGAAAATAGCCCTCGTGCACCGGAATAT
GTATTTAATGCTGGTGTACCAGTATTAGGCATTTGCTATGGAATGCAAACGATGGCGATGCAACTTGGCGGCTTAACCGA
AACGTCTGATCACAGAGAGTTCGGCTATGCTTCCGTTTCTCTTGAAAATTCCACCGCACTTTTTGCAAATCTTAACGATA
ATTTAACCGCTTCTGAGCCAAAATTAGACGTTTGGATGAGCCACGGCGATAAGGTAACGCGCTTACCAGAAAACTTCAAA
GTAACTGGCACAACGCTAACCTGCCCAATTGCTGCGATGTCTGATGAAAGCCGTCGTTTCTACGGTGTGCAGTTCCACCC
TGAAGTAACGCATACTAAAAAAGGCTTGGAATTATTAACCAACTTCGTAGTAAACATCTGTGGTTGCGAAACCAAATGGA
CAGCAGAAAACATTATCGAAGATGCCGTTGCTCGCATTAAAGAGCAAGTGGGCGATGATGAAGTGATTTTAGGCTTATCT
GGTGGTGTGGACTCTTCTGTGGTTGCATTACTTTTACACCGTGCTATCGGCAAAAACTTACACTGCGTATTTGTGGATAA
CGGTTTACTCCGCTTACACGAAGGCGACCAAGTCATGGAAATGTTTGGCGATAAATTCGGTTTAAACATCACTCGTGTTG
ATGCTGAAAGTCGTTTCTTAGGTGAACTTGCAGGCGTATCTGATCCTGAAGCGAAACGTAAAATTATCGGTAAAGTGTTC
GTGGATGTATTCGATGATGAATCGAAAAAACTCACTAATGTGAAATGGTTGGCACAAGGTACGATTTACCCTGACGTAAT
CGAATCTGCAGCAAGCAAAACTGGTAAAGCACATGTGATTAAATCACACCACAACGTAGGTGGCTTACCAGACTATATGA
AACTTGGTTTAGTTGAACCTTTACGTGAATTATTTAAAGATGAAGCTACGTAAAATCGGTTTAGCATTAGGCTTACCAGCT
GAAATGATCAACCGCCACCCATTCCCTGGCCCAGGCTTAGGTGTGCGTGTATTAGGCGAAGTGAAAAAAGAATACTGCGA
TTTATTACGCCGTGCGGATGCGATCTTTATCGAAGAATTACGCAACAGCGGTTGGTATGAAACTGTAGGTGTGATGGGCG
ATGGCCGTAAATACGATTGGGTTATTTCCCTACGCGCGGTAGAAACAATCGATTTTATGACCAAACCAGCCAAGCCTTCA
GCGTATTCTTACCAGTGAAATGCACATTGGGCACATTTGCCTTATGATTTATTAGGCAAAGTGTCTAACCGTATCATCAA
CGAAGTGAATGGAATTTCCCGCGTCGTATACGACATCAGCGGAAAACCACCCGCAACAATCGAGTGGGAATAA

FIG.5

METHOD FOR IDENTIFYING SUB-SEQUENCES OF INTEREST IN A SEQUENCE

CROSS REFERENCE TO RELATED APPLICATIONS

This application is a divisional of patent application Ser. No. 10/858,744, entitled "Method for Identifying Sub-Sequences of Interest in a Sequence", filed Jun. 2, 2004, now abandoned, which is herein incorporated by reference in its entirety for all purposes.

REFERENCE TO SEQUENCE LISTING

The present application contains a Sequence Listing of SEQ ID NO 1 and SEQ ID NO 2, which is herein incorporated by reference in its entirety. The respective Sequence Listing is identical to the submitted Sequence Listing filed with U.S. application Ser. No. 10/858,744, filed on Jun. 2, 2004, of which the present case is a divisional filing.

BACKGROUND

The invention relates generally to algorithmic information theory, and more specifically, to the identification of sequences of interest in a given data series.

In various applications, such as information theory, data compression, and intrusion detection, it may be desirable to identify sequences of interest within a data series. It may be advantageous to identify such sequences of interest in order to extract meaningful information from the identified sequences or to allow easier manipulation or analysis of the data series. For example, identification of repetitive sequences in a data series may allow easier or more effective compression of the data.

Similarly, in the field of genetics, biologically interesting phrases or sequences in a genome, such as the human genome, may have higher redundancy than non-meaningful phrases, as nature tends to repeat or emphasize important sequences more frequently than unimportant sequences. However, for the genomes, which are known or are being sequenced, the purposes of different parts of the genomes are currently unknown. Hence, the identification of meaningful or interesting sequences within a genome may pose a challenge.

Furthermore, it is increasingly difficult to identify meaningful sequences of interest employing traditional techniques. In particular, the vast amount of data, such as genome data is difficult to analyze using traditional techniques in a computationally efficient manner. In addition, existing computational techniques to determine meaningful information may be inadequate for the identification of sequences of interest. For example, existing techniques may fail to identify DNA sequences in a genome that are known to be of interest, such as sequences experimentally demonstrated to be of interest. Hence, it may be desirable to develop techniques that efficiently and accurately recognize sequences of interest within a data series.

BRIEF DESCRIPTION

Briefly, in accordance with one embodiment of the present technique a method for identifying a sequence of interest is presented. The method includes analyzing a data series based on a grammar comprising at least an initial grammar. A statistical heuristic is calculated for each sub-sequence of the analyzed data series. A selected statistical heuristic is compared with one or more reference conditions. The grammar and the data series are updated with a symbol representing a sequence corresponding to the selected statistical heuristic based upon a non-termination result of the comparison. Alternatively, the sequence is identified as a sequence of interest based upon a termination result of the comparison. Code stored on tangible, machine-readable media may afford functionality of the type defined by these methods and is provided for by the present technique.

In accordance with another embodiment of the present technique, a method is provided for processing a data series. The method comprises the step of specifying a data series for analysis. One or more routines configured to analyze the data series based on minimum description length principles are executed. The analyzed data series comprising at least one sequence of interest is obtained.

In accordance with a further embodiment of the present technique, a method is provided for identifying a biological sequence of interest. The method comprises analyzing a biological polymer sequence based on a grammar comprising at least an initial grammar. A minimum description length heuristic for each sub-sequence of the analyzed biological polymer sequence may be calculated. A selected minimum description length heuristic may be compared with one or more reference conditions. The grammar and the biological polymer sequence may be updated with a symbol representing a sub-sequence corresponding to the selected minimum description length heuristic based upon a non-termination result of the comparison. Alternatively, the sub-sequence may be identified as a biological sequence of interest based upon a termination result of the comparison. Code stored on tangible, machine-readable media may afford functionality of the type defined by these methods and is provided for by the present technique.

DRAWINGS

These and other features, aspects, and advantages of the present invention will become better understood when the following detailed description is read with reference to the accompanying drawings in which like characters represent like parts throughout the drawings, wherein:

FIG. 5 depicts identified repetitive sequences in a genome sequence, in accordance with one aspect of the present technique.

DETAILED DESCRIPTION

In many fields, such as genomic sequencing and analysis, it may be desirable to identify repetitive sequences, either to assist in compression and manipulation or to facilitate analysis. In particular, it may be desirable to identify such sequences in a computationally efficient manner. The techniques discussed herein address some or all of these issues.

Figure 1:
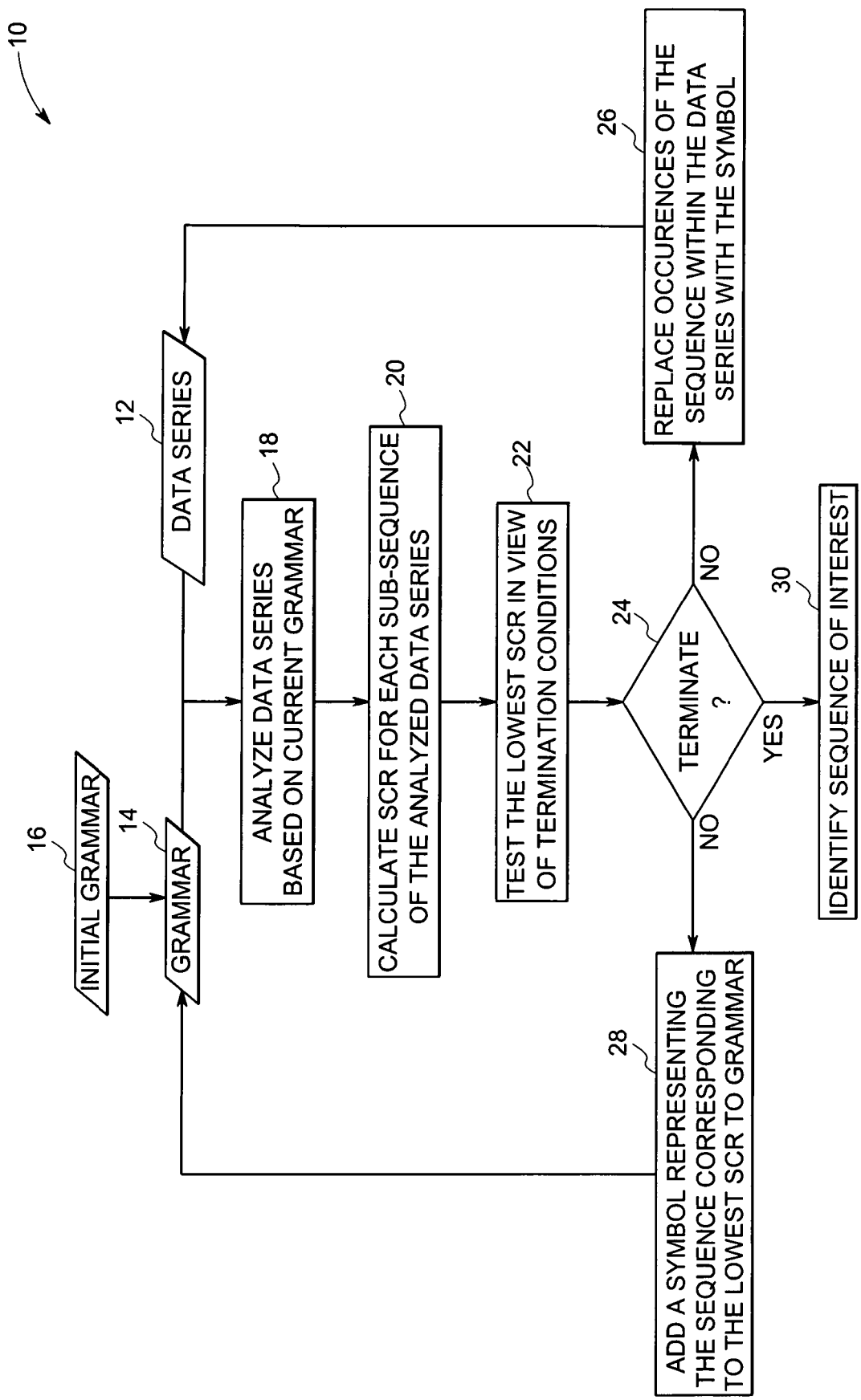
FIG. 1 is a flowchart depicting steps for identifying a sequence of interest from a data series, in accordance with one aspect of the present technique.

Turning now to the drawings, and referring to FIG. 1, a flow chart 10 depicts steps for identifying a sequence of interest, according to one aspect of the present technique. As suggested by the flow chart 10, a given data series 12 may be provided, within which may be one or more sequences of interest to be identified. The data series 12 may be constructed from a grammar 14. As will be appreciated by those of ordinary skill in the art, a grammar 14 may comprise terminals, i.e., uncombined symbols, and variables, i.e., combinations of terminals or terminal and other variables. For example, for a numeric data series 12, the grammar may include the numerals 0-9 as terminals and combinations of the terminals as variables. Similarly, an alphanumeric data series 12 may include numerals 1-9, the alphabetic letters, punctuation marks, and so forth as terminals and combinations of the terminals as variables. In other words, the grammar generally defines the characters or symbols, either alone or in combination, which may be found within the data series. In the context of biological sequences, such as deoxyribonucleic acid (DNA) sequences and ribonucleic acid (RNA) sequences or peptide sequences, the grammar 14 may include symbols representing nucleotides and amino acids, respectively. As will be discussed herein, the grammar 14 and the data series 12 may be updated in the process of trying to identify sequences of interest. Initially, however, the grammar 14 includes at least an initial grammar 16 encompassing the characters or symbols of which the data series 12 is initially comprised, i.e., the initial "alphabet." Furthermore, as will be appreciated by one of ordinary skill in the art, the grammar may also be known as a codebook or model in the art.

Once the data series 12 and grammar 14 are established, the method for identifying a sequence of interest begins at step 18, where the analysis of the data series 12 based on the grammar 14 is performed. In accordance with one embodiment of the present technique, analysis of the data series 12 involves partitioning the data series 12 into symbols or phrases that contribute most to the compression of the data series 12. Furthermore, the analysis of the data series 12 may be based upon algorithmic minimum sufficient statistics, such as, but not limited to, Kolmogorov Complexity.

For simplicity, the example of Kolmogorov Complexity will be discussed herein, though one of ordinary skill in the art will appreciate that other algorithmic minimum sufficient statistics may be equally applicable to the present discussion and techniques. With regard to Kolmogorov Complexity the descriptive complexity contained in a data series 12 is measured. However, one of the drawbacks associated with Kolmogorov Complexity is that it is not computable.

This drawback may be addressed by dividing the data series 12 into a two-part code or description in which the first part represents regularity in the data series 12 and the second part represents the random part of the data series 12. For example, the first part of the code may be a description of a smallest set S containing the data series 12, and the second part an enumeration of the data series 12 within the finite set S. In this example, if the data series 12 is a typical, that is, random, member of the finite set S then its index or enumeration within the set may be incompressible. However, if the data series 12 is not a typical member of set S, that is, is not random, then this regularity may be employed to form a smaller set of which the data series 12 is an element. A formal representation of these notions may generally, be represented via a Kolmogorov Structure Function, which defines a smallest set S that may be described in at most k bits containing the data sequence x of length n. The Kolmogorov Structure Function may be defined as follows:

$$K_k(x^n \mid n) = \min_{\substack{p:\, l(p) \leq k,\, U(p,n)=S \\ x^n \in S \subseteq \{0,1\}^*}} \{\log|S|\} \quad (1)$$

where K represents the Kolmogorov Complexity of the data series 12. Equation (1) may be referred to as a Kolmogorov Minimum Sufficient Statistic.

As noted above, in general, the Kolmogorov Complexity is not computable. Hence, the ability to apply this parameter to the analysis of a data series 12 is based upon the use of estimators, such as, for example, the Minimum Description Length (MDL) coding technique. The estimation of the Kolmogorov Complexity using the MDL coding technique, typically comprises encoding the data series 12 as a hypothesis or model that identifies a presumptive distribution from which the data series 12 originated, appended with the data series 12 that is coded in an optimal way. In other words, the length of an MDL message is determined as follows:

$$L(M) = L(H) + L(D) \quad (2)$$

where L(M) is a message length, L(H) is a length of a specification of a hypothesis regarding the data series 12, and L(D) is a length of the data series 12, encoded in an optimal manner given hypothesis H. Generally, MDL coding approaches the Kolmogorov Complexity or actual bound on the minimum length required for representing a data series 12.

As discussed above, the two-part description consists of a model that describes regularity associated with the data series 12 and a data portion describing the random elements of the data series 12. The sum of the lengths of these two parts is equal to the Kolmogorov Complexity of the data series 12. In general, many two-part code descriptions of a data series 12 may exist, with the shortest being termed the Algorithmic Minimum Sufficient Statistic. Among the possible two-part descriptions of the data series 12, the combination that minimizes a two-part descriptive cost, that is, provides the shortest or most compressed description, may be termed as an MDL description.

By means of example, an MDL decomposition of a data series x, where the data series may be a binary string, may be represented by:

$$K_\phi(x) = {}^+ K(S) + \log_2(|S|) \quad (3)$$

where $K_\phi(x)$ represents the Kolmogorov Complexity, S represents a finite set of which x is a typical, that is, equally likely, element. The symbol $=^+$ is employed to indicate that both $<^+$ and $>^+$ are true, where the symbol $<^+$ is utilized to denote an inequality with an additive constant. The minimum possible sum of a descriptive cost for set S and the logarithm of the cardinality of the set corresponds to an MDL two-part description for data series (string) x.

Keeping in mind the preceding discussion of complexity estimation, one of ordinary skill in the art will appreciate that is may be desirable to partition the data series 12 of FIG. 1 into symbols that provide a near optimal compression among possible partitions. In order to achieve this a Symbol Compression Ratio (SCR) heuristic may be employed to evaluate the contribution of an individual symbol to overall compression ratio between different partitions. Furthermore, the SCR heuristic may be recursively implemented as an Optimal Symbol Compression Ratio (OSCR) algorithm to estimate the complexity of the data series 12. This compression technique estimates the Kolmogorov Complexity via the MDL technique described above by recursively modeling the data series 12 as a concatenation of a finite set of symbols. In this manner, the OSCR algorithm recursively forms a minimum sufficient algorithmic statistic consisting of a grammar defining a set to which a sequence of interest is a typical element. In other words, the OSCR algorithm allows the identification of one or more repeated sequences within the data series 12 which may be of interest due to their degree of repetition.

The effect of a partition based on MDL, as described above, may be studied by examining the entropy of the distribution of symbols. The entropy of the distribution of symbols, $H_s$, defines the average per symbol compression bound in bits per symbol for a prefix free code. For a distribution p of I symbols, the entropy may be defined as:

$$H_s = -\sum_i p_i \log_2(p_i). \qquad (4)$$

The entropy may be used in the optimization of the partition (the number of symbols, their length, and distribution) of the data series 12 such that the compression bound plus the grammar size is minimized according to the MDL criteria. In particular, the compression bound is defined by the product, $R*H_s$, where R represents the total number of repetitions. The size of the grammar, that is the model descriptive cost, M, (also known as descriptive length), may be estimated as the sum of the lengths of unique symbols:

$$M = \sum_i l_i \qquad (5)$$

where $l_i$ is the length of symbol i. Furthermore, an estimate of the total descriptive length $D_p$ may be computed as:

$$D_p = M + R \cdot H_s \qquad (6)$$

where R is the total number of repetitions, and $H_s$ is the entropy.

Typically, in seeking to partition the data series 12 to minimize the total string descriptive cost $D_p$, the factors considered are the length that the presence of each symbol adds to the total descriptive length and the amount of coverage of the total string length L that it provides. Thus, the descriptive length of the data series 12 under partition p may be defined as:

$$D_p = R\log_2(R) + \sum_i [l_i - r_i \log_2(r_i)] \qquad (7)$$

where R is the number of repetitions, $l_i$ is the length of symbol i, and $r_i$ is the number of repetitions of symbol i in data series 12. A per symbol descriptive cost may be estimated by employing the following equations:

$$R\log_2(R) = \sum_i r_i \log_2(R) = \log_2(\hat{R}) \sum_i r_i \qquad (8)$$

where $\hat{R}$ is a constant for a given partition.

In a recursive implementation, such as may be employed in one implementation of the present technique, $\hat{R}$ may be computed from a known partition p and the length and number of repetitions of the candidate symbol i. Thus, $$d_i = r_i(\log_2(\hat{R}) - \log_2(r_i)) + l_i \qquad (9)$$

where $d_i$ is the descriptive cost of symbol i, $l_i$ is the length of symbol i, and $r_i$ is the number of repetitions of symbol i in data series 12. Equation (9) represents a metric that may be employed to estimate the descriptive cost of any possible symbol in the data series 12.

A measure of an MDL based heuristic for a particular symbol, may be represented by the descriptive length of the data series 12 divided by the length of the data series 12 covered by this symbol. For example, an MDL based heuristic, such as the Symbol Compression Ratio (SCR) may be defined by the following equation:

$$\lambda_i = \frac{d_i}{L_i} = \frac{r_i(\log_2(\hat{R}) - \log_2(r_i)) + l_i}{l_i r_i} \qquad (10)$$

where $\lambda_i$ represents the SCR, $d_i$ is the descriptive cost of symbol i, $L_i$ is the length of data series 12 consumed by symbol i, $l_i$ is the length of symbol i, $r_i$ is the number of repetitions of symbol i in the data series 12, and $\hat{R}$ is a constant for a given partition.

As discussed above, an algorithm, referred to herein as the Optimal Symbol Compression Ratio (OSCR) algorithm, may be based on the heuristic presented in equation (10) and may be utilized in processing the data series 12. This algorithm recursively forms a partition of the data series 12 (string x) into symbols that have the best SCR among possible symbols contained in x. The concept is to form a grammar dictionary that provides near optimal compression by adding one symbol at a time based upon the SCR of the symbol.

Referring again to FIG. 1, one method for identifying a sequence of interest is summarized in the flow chart of FIG. 1. The depicted method may employ the OSCR algorithm summarized above or other similar recursive techniques. As will be appreciated by those of ordinary skill in the art, the present technique is generally directed to finding a finite set of patterns from which a data series 12 is typical in the Kolmogorov Minimum Sufficient Statistic or MDL sense. The following paragraphs summarize exemplary steps that may be performed to analyze a data sequence in accordance with the present technique.

As depicted in FIG. 1, a data series 12 representing the input string x may be analyzed at step 18 based on the current grammar. The grammar 14 typically includes at least an initial grammar 16, where the initial grammar 16 may include an alphabet of terminals of size $N_{symbols}$. The $N_{symbols}$ may, for example, represent unique bytes encountered in the input data series 12. Additionally, a lexicographic ordering of this alphabet may be constructed, if desired, at step 18. Furthermore, an array $A_{index}$ representing the input data series 12 as an array of index values may also be constructed as part of the analysis of step 18.

A tree of non-overlapping sub-strings contained in input string x, that is, the data series 12, that occur more often than (or equal to) a threshold value is formed as a product of the analysis step 18, where each sub-string or a potential codeword for the grammar 14 may be represented as a node of the tree. In one implementation, the threshold value may represent twice the frequency of occurrence of the sub-string in the data series 12, though other thresholds are also possible. In addition, the frequency of occurrence of each of the sub-strings, may be noted during step 18. This may be accomplished by recursively searching the data series 12 for repetitions of the sub-strings and noting or storing the frequency of occurrence of each sub-string.

At step 20, a MDL based statistical heuristic, such as a SCR, for all the sub-sequences may be computed using equation (10), as described above. Furthermore, in the depicted example, a statistical heuristic such as the sub-string having the lowest SCR may be selected and stored, along with the corresponding sub-string length and the number of repetitions, as parameters, $\lambda_{select}$, $l_{select}$ and $r_{select}$ respectively.

At step 22, the lowest SCR, as determined above, may be tested in view of the desired termination conditions. For instance, the termination condition may be represented as follows:

$$(\lambda_{best} < 1) \cap (r_{select} \cdot l_{select} \cdot \lambda_{select} > G_{min}) \tag{11}$$

where $G_{min}$ is a configurable minimum value to ensure compression at each step, if desired. For example, the value of $G_{min}$ may be varied from zero to higher threshold values that may reduce the number of algorithm iterations.

Subsequently, at decision block 24, checks are performed to determine whether the termination criteria, such as the threshold of equation (11), have been satisfied. If the termination criteria have not been satisfied, steps 26 and 28 may be performed, allowing additional analysis and testing to occur until the termination criteria are met. For example, at step 26, all occurrences of the selected sub-string, that is, the sub-string having the lowest SCR, may be replaced within the data series 12 with a corresponding symbol. In this manner, the data series 12 may be simplified or compressed in view of the identified sub-string.

Similarly, at step 28, the grammar 14 may be updated to include the symbol, which will be present in the data series 12 in the next iteration of the process upon completion of step 26. In this manner, the recursive operation of the OSCR algorithm progressively adds symbols to the grammar based on the contribution of the symbols to the compression of the available candidates. The above steps of analyzing, calculating a statistical heuristic, comparing the lowest SCR, and updating the grammar 14 and the data series 12 may be recursively iterated through until a termination result is indicated at decision block 24. When a termination result is obtained at decision block 24, the current sub-string having the lowest SCR may be identified as a sequence of interest at step 30. As noted above, the sequence identified in this manner may be of interest because the repetition of the sequence suggests importance, such as may occur in biological polymers such as DNA, RNA, or amino acid sequences.

As will be appreciated by those of ordinary skill in the art, the data series 12 may be encoded using techniques, such as, Huffman and arithmetic coding. In such implementations, new indices relating to grammar sub-strings or grammar rules may be added and an array of symbols representing the data series 12 recomputed as variables are added to the grammar 14 through the recursions of the OSCR algorithm. In addition, the SCR heuristic, defined by equation (10), may be modified to accommodate the encoding of the model. The number of indices in the model, representative of the number of grammar terminals and grammar variables, relate directly to the model cost of a new codeword. Furthermore, as described herein, at each iteration of the algorithm symbols may be combined to form new codewords, which in turn may be represented by new symbols, which may in turn be incorporated into subsequent processing and analysis. If every index is considered to be equally likely, a model cost of $H_m = \log_2$ (max Index) bits for each symbol may be assigned. Furthermore, the cost of sending the Huffman code length for each symbol may be accounted for by sending one additional symbol. The SCR heuristic, accounting for the model cost $H_m$ in bytes may be redefined as follows:

$$\lambda_i = \frac{r_i(\log_2(\hat{R}) - \log_2(r_i))/8 + (l_i + 1) \cdot H_m}{l_i r_i H_m} \tag{12}$$

Figures 2, 3, 4:
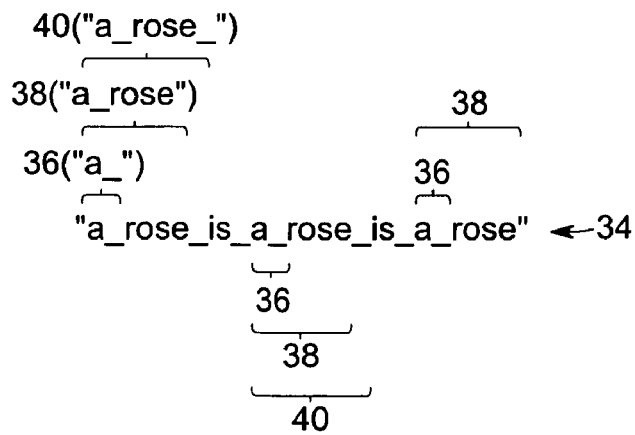
FIG. 2 illustrates the identification of a sequence of interest from a data series, in accordance with one aspect of the present technique.
FIG. 3 depicts a table representing symbols and corresponding frequencies of occurrence, in accordance with one aspect of the present technique.
FIG. 4 depicts a table representing a grammar model indices for encoding a grammar, in accordance with one aspect of the present technique.

An example employing the OSCR algorithm described above to identify a sequence of interest is provided by FIG. 2. As depicted in FIG. 2, the OSCR algorithm may be applied to identify a sequence of interest that may facilitate compression and estimation of the sophistication, where sophistication, as known to one of ordinary skill in the art, is a measure of meaningful information in a data series, of the given sample data series 34:

a_rose_is_a_rose_is_a_rose.

In this example, reference numerals 36, 38 and 40 represent sub-strings "a_", "a_rose" and "a_rose_" respectively.

Referring now to FIG. 3, a listing of an initial symbol alphabet and their corresponding frequencies of occurrence in the sample data series 34 are listed in table 42. A first column 44 of table 42 lists the initial symbol alphabet, or grammar, which includes seven terminals {a, _[space], r, o, s, e, i}. Furthermore, a second column 46 of table 42 represents the frequency of occurrence of each symbol.

An integer sequence representation of the data series 34, with terminal symbols replaced with a corresponding index value, may be depicted as:

| a | r | o | s | e | i | s | a | r | o | S | e | i | s | a | r | o | s | e |
|---|---|---|---|---|---|---|---|---|---|---|---|---|---|---|---|---|---|---|
| 1 | 2 | 3 | 4 | 5 | 6 | 2 | 7 | 5 | 2 | 1 | 2 | 3 | 4 | 5 | 6 | 2 | 7 | 5 | 2 | 1 | 2 | 3 | 4 | 5 | 6 |

Expanding the tree with sub-strings beginning with the terminal a illustrates that there are three occurrences of each of the sub-strings:

a, a_, a_r, a_ro, a_ros, a_rose.

However, only two occurrences of longer sub-strings, such as "a_rose_" 40, are present. For simplicity, this example is limited to the consideration of the sub-strings "a_" 36, "a_rose" 38 and "a_rose_" 40.

The initial tree statistics and SCR calculation may be computed by following the steps of the OSCR algorithm outlined above. For example, in the instance where the symbol i represents the sub-string "a_", the length, l, of symbol i, is 2. Moreover, the number of repetitions, r, of symbol i in the data series 34 would be 3. Additionally, the total number of repetitions, R, is computed to be 26. In a similar fashion, in the instance where "a_rose" is the symbol, the length, l, would be 6, the number of repetitions, r, would be 3, and the total number of repetitions, R, would be 11. Similarly, for the sub-string "a_rose_", the values of l, r and R would be 7, 2 and 14 respectively.

In addition to the computation of the parameters outlined above, the value of the SCR, $\lambda$, is computed for each symbol. For the symbol, "a_", $\lambda$ would be 1.023, as computed using equation (10). Similarly, for the sub-string "a_rose", $\lambda$ would be 0.500 and for the sub-string "a_rose_", $\lambda$ would be 0.7143.

As may be observed, the value of λ decreases as the length of the sub-string increases until the number of repetitions drops from 3 to 2. Since there exist only two repetitions of the phrase "a_rose_", the best, that is, the lowest, λ along this branch is $$\lambda_{best} = \frac{1}{2},$$

and the search may be terminated along this branch. Because the selection is based on the SCR, λ, the selection process does not necessarily select the most frequently repeated or the longest symbol, that is, sub-string. Instead the length of the sub-string and the amount of repetition are both factors, but not determinative factors, in the selection process. For instance, in this example, the selected codeword is:

$S_1 \rightarrow a\_rose$

After this selection, the model may be updated by the addition of this codeword. In addition, the instances of the sub-string "a_rose" in the sample data series 34 are replaced with the symbol $S_1$. Furthermore, replacing the sub-string "a_rose" with a corresponding symbol index of 8, an integer sequence representation of the data series 34, may be depicted as:

| $S_1$ | _ | i | s | _ | $S_1$ | _ | i | s | _ | $S_1$ |
|---|---|---|---|---|---|---|---|---|---|---|
| 8 | 2 | 7 | 5 | 2 | 8 | 2 | 7 | 5 | 2 | 8 |

Iterating through the algorithm a second time provides a second rule:

$S_2 \rightarrow is\_S_1$ which may, by updating the grammar, the sample data series 34, and the respective array and index, be represented as the array sequence:

| $S_1$ | $S_2$ | $S_2$ |
|---|---|---|
| 8 | 9 | 9 |

The resulting grammar may be summarized as follows:

$S_1 \rightarrow a\_rose, S_2 \rightarrow is\_S_1, S \rightarrow S_1S_2S_2.$

Additionally, the model may be summarized as:

$S_1 \rightarrow a\_rose\ f(S_1)=1$ $S_2 \rightarrow is\_S_1\ f(S_2)=2$ where f(S) represents the frequency of occurrence of each phrase.

Referring to FIG. 4, the grammar model indices for encoding of this grammar are summarized. The values in a first column of the table 48 represent the respective indices 50 corresponding to a symbol (terminal or variable). A second column of the table 48 represents a symbol array 52. For grammar terminals (index values 1 through 7) the symbol array is the ASCII code for the corresponding terminal. Furthermore, for grammar variables (index values 8 and 9), the symbol array 52 represents the grammar rule, constructing the phrase from indices corresponding to other terminals and variables. The separator symbol is added artificially and given an index of zero. Moreover, a third column of the table 48 represents a decoded phrase 54 corresponding to each symbol listed in the second column of the table 48.

Since there are only seven unique bytes in this grammar (alphabet), these ASCII symbols may be sent literally in seven bytes. The two codewords may be encoded as a sequence of eleven numbers with two additional separators. Huffman code lengths may be sent for each variable and terminal in lexicographic order, with a single bit assigned for phrase 8 and its complement for phrase 9.

The data series 34 may be illustrated as follows:

| Terminals | Codeword 1 | Codeword 2 | HuffCodelengths |
|---|---|---|---|
| 97 13 114 111 112 101 105 | 1 2 3 4 5 6 0 | 2 7 5 2 8 0 | 0 0 0 0 0 0 0 1 1 | and may be encoded using arithmetic coding and appended with the data portion of the code. The resulting model size, including a configuration byte, is 22.25 bytes. Thus, the entire encoded cost for the originally 26-byte sample data series 34 is 22.6 bytes. Hence, it may be inferred that, due to the high model cost compared to the data cost, there is significant pattern content in the sample data series 34.

As may be appreciated, the present techniques may be used to identify repetitive sequences within lengthy or large amounts of data. For example, an OSCR algorithm may be employed to identify sequences of interest in a given biological (or other) data series such as DNA sequences, RNA sequences, amino acid sequences, and so forth. For instance, in a case where a DNA sequence is the data series of interest, the analysis of the DNA sequence amounts to an analysis of the sequence of nucleotides forming the DNA. The nucleotide sequence is formed from a four-symbol alphabet, that is, four nucleotides, represented by the symbols {A, T, C, G} that form the genetic code. Generally, DNA sequences are very random in nature, and discerning structure may lead to attractive discoveries or important sequences within the genome.

As discussed above, a recursive process, such as may be implemented via an OSCR algorithm described herein, may be performed on the biological data series. Turning now to FIG. 5, a biological polymer sequence of interest 56 identified by the application of the present techniques is illustrated. In FIG. 5, the biological polymer sequence is represented by the H Influenza genomic sequence 58. During the analysis step, the H Influenza genomic sequence 58 represents the input biological polymer sequence x. The grammar may include an initial grammar, where the initial grammar may include an alphabet of terminals of size $N_{symbols}$. The $N_{symbols}$ may, for example, represent unique bytes encountered in the biological sequence 58, such as {A, T, C, G}. Additionally, a lexicographic ordering of this alphabet may be constructed. Furthermore, an array $A_{index}$ representing the input biological sequence 56 as an array of index values may also be constructed.

Based on a recursive analysis, as set forth above, repetitive sequences of DNA in the H influenza genome may be identified, such as repeated sequence 60 of FIG. 5. In particular, the OSCR algorithm identifies the repeated sequences 60 that are present within the DNA sequences HI0221, HI0221.1 and HI0222, which form part of the H influenza genome. While the repeated sequences 60 are known to be of interest, the ease with which they are identified by application of the OSCR algorithm, suggests that application of such an algorithm may greatly facilitate identification of new and important repeated sequences in a computationally efficient manner.

As will be appreciated by those of ordinary skill in the art, the foregoing example, demonstrations, and process steps may be implemented by suitable code on a processor-based system, such as a general-purpose or special-purpose computer. It should also be noted that different implementations of the present technique may perform some or all of the steps described herein in different orders or substantially concurrently, that is, in parallel. Furthermore, the functions may be implemented in a variety of programming languages, such as C++ or JAVA. Such code, as will be appreciated by those of ordinary skill in the art, may be stored or adapted for storage on one or more tangible, machine readable media, such as on memory chips, local or remote hard disks, optical disks (that is, CD's or DVD's), or other media, which may be accessed by a processor-based system to execute the stored code. Note that the tangible media may comprise paper or another suitable medium upon which the instructions are printed. For instance, the instructions can be electronically captured via optical scanning of the paper or other medium, then compiled, interpreted or otherwise processed in a suitable manner if necessary, and then stored in a computer memory.

The method described herein of identifying sequences of interest, given an input data sequence based on MDL principles enables the implementation of a universal compression algorithm capable of universal complexity as well as sophistication estimation. As described herein, the present techniques may be used to identify repetitive sequences, which may be of interest in a variety of fields, such as cryptography or biological research. In particular, any field in which pattern recognition is a component may benefit from the techniques described herein.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A tangible, machine-readable media, comprising:
   code adapted to analyze a data sequence, consisting essentially of a plurality of symbols, based on a grammar comprising at least an initial grammar, wherein the grammar defines at least the plurality of symbols contained within the data sequence;
   code adapted to partition the data sequence into a plurality of sub-sequences and to calculate a statistical heuristic for each sub-sequence of the analyzed data sequence;
   code adapted to compare a selected statistical heuristic of a selected sub-sequence with one or more reference conditions, and to yield a termination result if the selected statistical heuristic is beyond a threshold defined by the one or more reference conditions or a non-termination result otherwise;
   code adapted to update the grammar and the data series with a symbol representing the selected sub-sequence based upon the non-termination result of the comparison; and
   code adapted to identify the selected sub-sequence as a sequence of interest based upon the termination result of the comparison.

2. The tangible medium, as recited in claim 1, comprising code adapted to iterate the steps of analyzing, calculating, comparing, and updating until the termination result of the comparison occurs.

3. The tangible medium, as recited in claim 1, wherein the code adapted to calculate the statistical heuristic for each sub-sequence computes the statistical heuristic using a minimum sufficient statistics algorithm.

4. The tangible medium, as recited in claim 1, wherein the code adapted to calculate the statistical heuristic for each sub-sequence computes a symbol compression ratio using an optimal symbol compression ratio algorithm.

5. The tangible medium, as recited in claim 1, wherein the statistical heuristic comprises a minimum description length heuristic and wherein the selected statistical heuristic comprises the minimum description length heuristic having the lowest value.

6. The tangible medium, as recited in claim 1, wherein the statistical heuristic comprises a symbol compression ratio and wherein the selected statistical heuristic comprises the symbol compression ratio having the lowest value.

7. A tangible, machine-readable media, comprising:
   code adapted to analyze a biological polymer sequence, consisting essentially of a plurality of symbols, based on a grammar comprising at least an initial grammar, wherein the grammar defines at least the plurality of symbols contained within the biological polymer sequence;
   code adapted to partition the biological polymer sequence into a plurality of sub-sequences and to calculate a minimum description length heuristic for each sub-sequence of the analyzed biological polymer sequence;
   code adapted to compare a selected minimum description length heuristic corresponding to a selected sub-sequence with one or more reference conditions, and to yield a termination result if the selected minimum description length heuristic is beyond a threshold defined by the one or more reference conditions or a non-termination result otherwise;
   code adapted to update the grammar and the biological polymer sequence with a symbol representing the selected sub-sequence based upon the non-termination result of the comparison; and
   code adapted to identify the selected sub-sequence as a biological sequence of interest based upon the termination result of the comparison.

8. The tangible medium, as recited in claim 7, comprising:
   code adapted to iterate the steps of analyzing, calculating, comparing, and updating until the termination result of the comparison occurs.

9. The tangible medium, as recited in claim 7, wherein the minimum description length heuristic comprises a symbol compression ratio and the selected minimum description length heuristic comprises the symbol compression ratio having the lowest value.

* * * * *

SEQUENCE LISTING

<160> NUMBER OF SEQ ID NOS: 2

<210> SEQ ID NO 1
<211> LENGTH: 1617
<212> TYPE: DNA
<213> ORGANISM: Haemophilus influenzae

<400> SEQUENCE: 1

```
atgtcattac gcattaaaca agaagccctt acttttgacg atgttctact cgtcccagct      60
cactcaactg tgcttccaaa tactgccaac ctttcaactc aacttactaa agaaattcgt     120
ttaaatatcc caatgctttc agcagcaatg gataccgtaa ctgaaaccaa acttgcgatc     180
tctttagcac aagaaggcgg tattggcttt attcataaaa atatgacgat cgaacgccaa     240
gcagatcgcg tgcgtaaagt aaaaaaattc gaaagtggta tcgtttctga accagtaact     300
gttttaccaa atttaacgct tgccgaactt gctgaaatgg tgaagaaaaa cggatttgcg     360
ggctaccctg ttgtagatgg ggaaaataat ttaatcggta tcattactgg ccgtgataca     420
cgtttcgtaa aagatttaag caaaacagtt tcacaagtaa tgacgaaaaa agaagacttg     480
gtgaccgtaa aagaaggggc gagtcgcgaa gaaattttgg aattaatgca tcaacaccgt     540
gttgaaaaag tattagtggt taatgatagt ttcaaactta aaggtatgat taccgttaaa     600
gacttccaaa aagcagaaca aaaaccaaat gcatgtaaag atgaattcgg tcgtttacgt     660
gtcggtgcgg ctgtaggtgc aggtgctggc aacgaagaac gtattgatgc cttagtgaaa     720
gcaggcgtag atgtactatt aattgattct tctcacggtc actcagaagg cgtattacaa     780
cgcgttcgtg aaactcgtgc aaaatatcca aatttgccta tcgttgcagg taacgtagca     840
acggctgaag gcgcaattgc attagcagac gcaggtgcaa gtgctgtaaa agtaggtatt     900
ggtcctggtt caatttgtac aactcgtatt gtaactggcg taggtgttcc acaaattacc     960
gctatcgcag atgcagctgc tgcattaaaa gatcgtggta ttcctgtaat tgctgacggt    1020
ggtatccgtt tctctggcga tattgcaaaa gctatcgctg ctggtgcaag ctgtgtaatg    1080
gttggctcga tgtttgcggg tacagaagag gctccaggtg aaatcgaact ttatcaaggt    1140
cgtgcattta aatcttaccg tggtatgggc tcattaggtg ccatggcgaa aggctcatca    1200
gaccgttatt tccaatcgga taacgcggca gataaactcg taccggaagg tattgaaggc    1260
```

| | |
|---|---|
| cgtattccat ataaaggtta cttaaaagaa atcatccacc aacaaatggg tggcttacgt | 1320 |
| tcttgtatgg gcttaacggg ctgtgcaact attgatgaac tacgcaccaa agcggaattt | 1380 |
| gttcgcatta gcggtgcagg cattaaagaa agccacgttc acgatgttgc tattactaaa | 1440 |
| gaagcaccta actatcgtat gggctaaatg acaaatatcc actatcacaa atcctaatc | 1500 |
| ctcgactttg gttcacaata cactcaactg attgcgcgtc gtgtgcgtga atcggtgtg | 1560 |
| tactgcgaac tttgggcttg ggatgtaacc gaacaaaaat ccgtgaattt gctcccg | 1617 |

<210> SEQ ID NO 2
<211> LENGTH: 1913
<212> TYPE: DNA
<213> ORGANISM: Haemophilus influenzae

<400> SEQUENCE: 2

| | |
|---|---|
| aactttatca aggtcgtgca tttaaatctt accgtggtat gggctcatta ggtgccatgg | 60 |
| cgaaaggctc atcagaccgt tatttccaat cggataacgc ggcagataaa ctcgtaccgg | 120 |
| aaggtattga aggccgtatt ccatataaag gttacttaaa agaaatcatc caccaacaaa | 180 |
| tgggtggctt acgttcttgt atgggcttaa cgggctgtgc aactattgat gaactacgca | 240 |
| ccaaagcgga atttgttcgc attagcggtg caggcattaa agaaagccac gttcacgatg | 300 |
| ttgctattac taaagaagca cctaactatc gtatgggcta aatgacaaat atccactatc | 360 |
| acaaatcct aatcctcgac tttggttcac aatacactca actgattgcg cgtcgtgtgc | 420 |
| gtgaaatcgg tgtgtactgc gaactttggg cttgggatgt aaccgaacaa caaatccgtg | 480 |
| aatttgctcc aacgggtatc attctttctg gcagtcctga agcacaact gaagaaaata | 540 |
| gccctcgtgc accggaatat gtatttaatg ctggtgtacc agtattaggc atttgctatg | 600 |
| gaatgcaaac gatggcgatg caacttggcg gcttaaccga acgtctgat cacagagagt | 660 |
| tcggctatgc ttccgtttct cttgaaaatt ccaccgcact ttttgcaaat cttaacgata | 720 |
| atttaaccgc ttctgagcca aaattagacg tttggatgag ccacggcgat aaggtaacgc | 780 |
| gcttaccaga aaacttcaaa gtaactggca caacgctaac ctgcccaatt gctgcgatgt | 840 |
| ctgatgaaag ccgtcgtttc tacggtgtgc agttccaccc tgaagtaacg catactaaaa | 900 |
| aaggcttgga attattaacc aacttcgtag taaacatctg tggttgcgaa accaaatgga | 960 |
| cagcagaaaa cattatcgaa gatgccgttg ctcgcattaa agagcaagtg ggcgatgatg | 1020 |
| aagtgatttt aggcttatct ggtggtgtgg actcttctgt ggttgcatta ctttttacacc | 1080 |
| gtgctatcgg caaaaactta cactgcgtat ttgtggataa cggtttactc cgcttacacg | 1140 |
| aaggcgacca agtcatggaa atgtttggcg ataaattcgg tttaaacatc actcgtgttg | 1200 |
| atgctgaaag tcgtttctta ggtgaacttg caggcgtatc tgatcctgaa gcgaaacgta | 1260 |
| aaattatcgg taaagtgttc gtggatgtat cgatgatga atcgaaaaaa ctcactaatg | 1320 |
| tgaaatggtt ggcacaaggt acgatttacc ctgacgtaat cgaatctgca gcaagcaaaa | 1380 |
| ctggtaaagc acatgtgatt aaatcacacc aaacgctagg tggcttacca gactatatga | 1440 |
| aacttggttt agttgaacct ttacgtgaat tatttaaaga tgaagtacgt aaaatcggtt | 1500 |
| tagcattagg cttaccagct gaaatgatca accgccaccc attccctggc ccaggcttag | 1560 |
| gtgtgcgtgt attaggcgaa gtgaaaaaag aatactgcga tttattacgc cgtgcggatg | 1620 |
| cgatctttat cgaagaatta cgcaacagcg gttggtatga aactgtaggt gtgatgggcg | 1680 |
| atggccgtaa atacgattgg gttatttccc tacgcgcggt agaaacaatc gatttttatga | 1740 |
| ccaaaccagc caagccttca gcgtattctt accagtgaaa tgcacattgg gcacatttgc | 1800 |

```
cttatgattt attaggcaaa gtgtctaacc gtatcatcaa cgaagtgaat ggaatttccc    1860
gcgtcgtata cgacatcagc ggaaaaccac ccgcaacaat cgagtgggaa taa           1913
```